(12) United States Patent
Zeman et al.

(10) Patent No.: US 7,135,497 B1
(45) Date of Patent: Nov. 14, 2006

(54) TREATING NEURAL CONDITIONS RESULTING FROM SPINAL CORD CONTUSIONS AND OTHER CAUSES

(75) Inventors: Richard J. Zeman, New York, NY (US); Joseph D. Etlinger, Mt. Kisco, NY (US)

(73) Assignee: New York Medical College, Valhalla, NY (US)

( * ) Notice: Subject to any disclaimer, the term of this patent is extended or adjusted under 35 U.S.C. 154(b) by 0 days.

(21) Appl. No.: 09/611,652

(22) Filed: Jul. 7, 2000

(51) Int. Cl.
*A61K 31/205* (2006.01)
*A61K 31/135* (2006.01)

(52) U.S. Cl. .................. 514/555; 514/649; 514/651; 514/653; 514/650

(58) Field of Classification Search ............ 514/555, 514/649, 650, 651, 653
See application file for complete search history.

(56) References Cited

U.S. PATENT DOCUMENTS 5,281,607 A  *  1/1994  Stone et al. .............. 514/280

FOREIGN PATENT DOCUMENTS

WO     WO99/09966     *  3/1999

OTHER PUBLICATIONS

Zeman et al., Experimental neurology 1999; 159:267-273.*
Sayers et al., Society for Neuroscience Abstracts 1998; 24: abstract 125.2.*
Zeman et al., Experimental Neurology, 1999;159:267-273.*
Murphy et al., Arch. Phys. Med. Rehabil., 1999;80(10):1264-1267.*
Vaidyanathan et al., Spinal Cord, 1996; 34: 691-695.*

* cited by examiner

*Primary Examiner*—San-ming Hui
(74) *Attorney, Agent, or Firm*—Amster, Rothstein & Ebenstein LLP

(57) ABSTRACT

$\beta_2$-agonists, such as clenbuterol and salbutamol can enhance the recovery of locomotive function and/or neuromuscular strength following spinal cord injuries or as a result of degenerative neural conditions such as Mnd. Pharmacological compositions for treating spinal cord injuries and degenerative neural conditions are also provided.

20 Claims, 9 Drawing Sheets

TREATING NEURAL CONDITIONS RESULTING FROM SPINAL CORD CONTUSIONS AND OTHER CAUSES

BACKGROUND OF THE INVENTION

The invention relates generally to treatments with $\beta_2$-agonists, such as treating neural conditions caused by spinal cord injuries and other causes, such as degenerative diseases, and more particularly to drugs and treatment methods which enhance the recovery of locomotor function and neuromuscular strength following spinal cord injuries or which result from other neurological conditions.

The spinal cord often responds to injury with profound loss of neuronal tissue and functional capacity. This can lead to significant loss of locomotor function. The same result can be caused by various neural conditions, such as motor neuron degeneration (mnd). For this reason, an important goal of rehabilitation following spinal cord injury or in the treatment of neurological conditions is to increase neuromuscular strength and function.

Prior treatments of spinal cord injuries have not been shown to be fully satisfactory and accordingly, it is desireable to provide improved treatment methods which can speed the recovery of the victim of a spinal cord injury, such as speeding the recovery of locomotor function and neuromuscular strength. A variety of agents including free radical scavengers, cyclooxygenase inhibitors, lipopolysaccharides, several steroids, calcium chelators, hypothermia, x-irradiation as well as surgical implants, that contain growth factors, have been shown to promote recovery based on various animal experiments. (See, e.g., Albin, M. S., R. J. White, G. Acosta-Rua, and D. Yashon, 1968, Study of functional recovery produced by delayed localized cooling after spinal cord injury in primates, J. Neurosurg. 29:113–120; Cheng, H., Y. Coa, and L. Olson. 1996, Spinal cord repair in adult paraplegic rats: Partial restoration of hind limb function, Science 273:510–513; Guth, L., Z. Zhang, and E. Roberts, 1994, Key role for pregnenolone in combination therapy, that promotes recovery after spinal cord injury, Proc. Natl. Acad. Sci. USA 91:12308–12312; Haghighi, S. S. ED. Hall, X. Z. Geng, J. J. Oro. and G. C. Johnson, 1993, Therapeutic value of 21-aminosteriod U74389F in acute spinal cord injury, Neurol. Res. 15:321–326; Kalderon. N., and Z. Fuks. 1996, Severed corticospinal axons recover electrophysiologic control of muscle activity after x-ray therapy in lesioned adult spinal cord, Proc. Natl. Acad. Sci. USA 93:11185–11190; and Kudo. Y. K. Takeda, and K. Yamazaki, 1990, Quin2 protects neurons against cell death due to $Ca^{2+}$ overload, Brain Res. 528:48–54, all incorporated by reference. However, these countermeasures may be incompletely effective, difficult to administer or costly. Because of such limitations, additional or alternative agents, particularly of a pharmacological nature, that can be used in spinal cord injured patients or patients suffering from neurological diseases are needed.

Accordingly, it is desireable to provide improved treatments for neural conditions resulting from injury and other causes.

SUMMARY OF THE INVENTION

Generally speaking, in accordance with the invention, $\beta_2$-agonists, such as clenbuterol and salbutamol can enhance the recovery of locomotive function and/or neuromuscular strength following spinal cord injuries or as a result of degenerative neural conditions such as Mnd. Pharmacological compositions for treating spinal cord injuries and degenerative neural conditions are also provided.

Accordingly, it is an object of the invention to provide an improved treatment for spinal cord injuries.

It is another object of the invention to provide an improved treatment for degenerative neurological conditions.

Another object of the invention is to provide a drug which can be administered to the victim of a spinal cord injury or neurological condition and speed the recovery of such injury.

The invention accordingly comprises the several steps and the relationship of one or more of such steps with respect to each of the others, and the composition possessing the characteristics, properties and the relation of constituents which are adapted to effect such steps, all as exemplified in the following detailed disclosure, and the scope of the invention will be indicated in the claims.

BRIEF DESCRIPTION OF THE DRAWINGS

For a fuller understanding of the invention, references had to the following description, taking in connection with the accompanied drawings, in which.

A significant linear relationship (P<0.0005) between % spared area and final BBB score was found by regression analysis.

Figure 6:
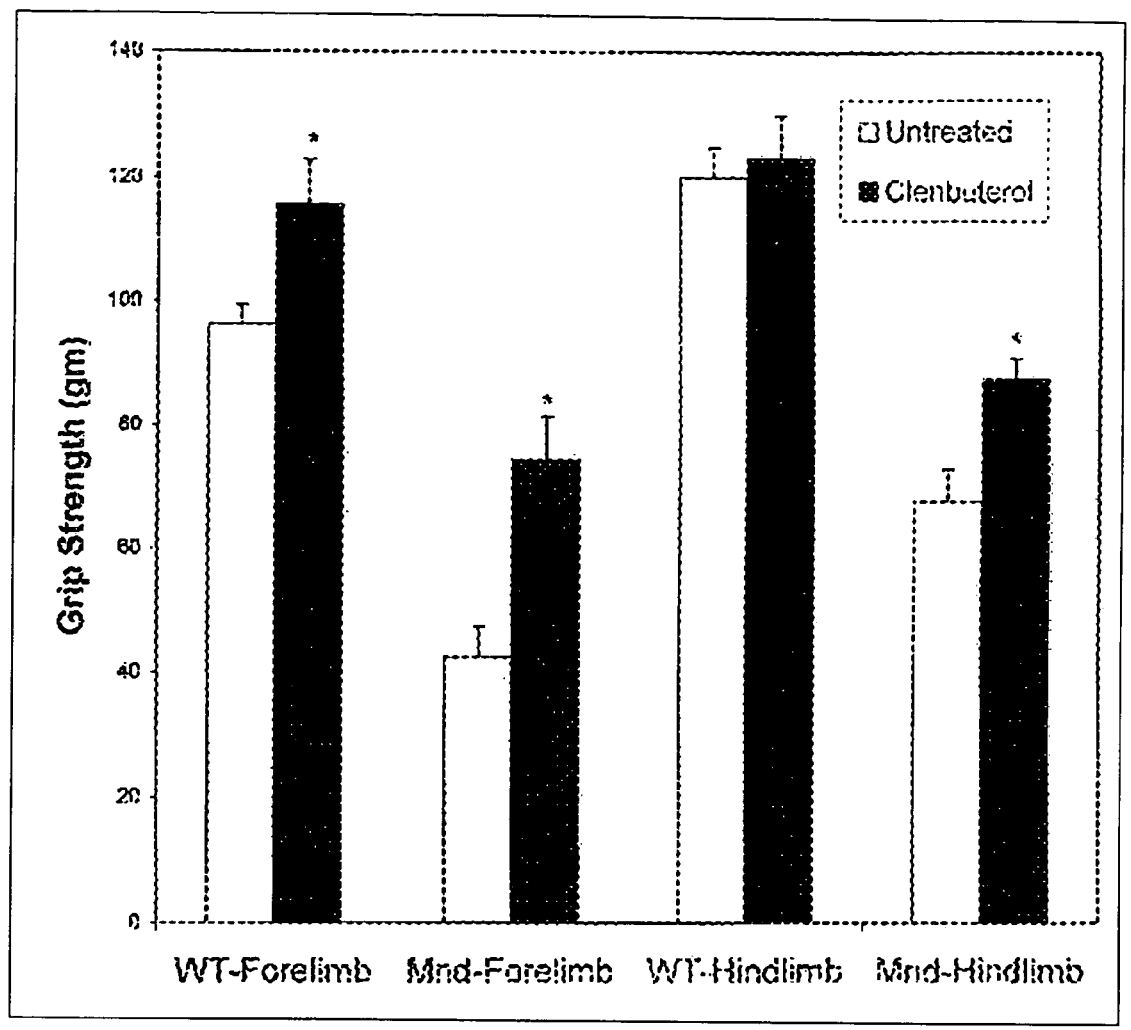

FIG. 6 is a graph showing the effects of clenbuterol on locomotor deficits in motor neuron degeneration (mnd) mice.

Figure 7:
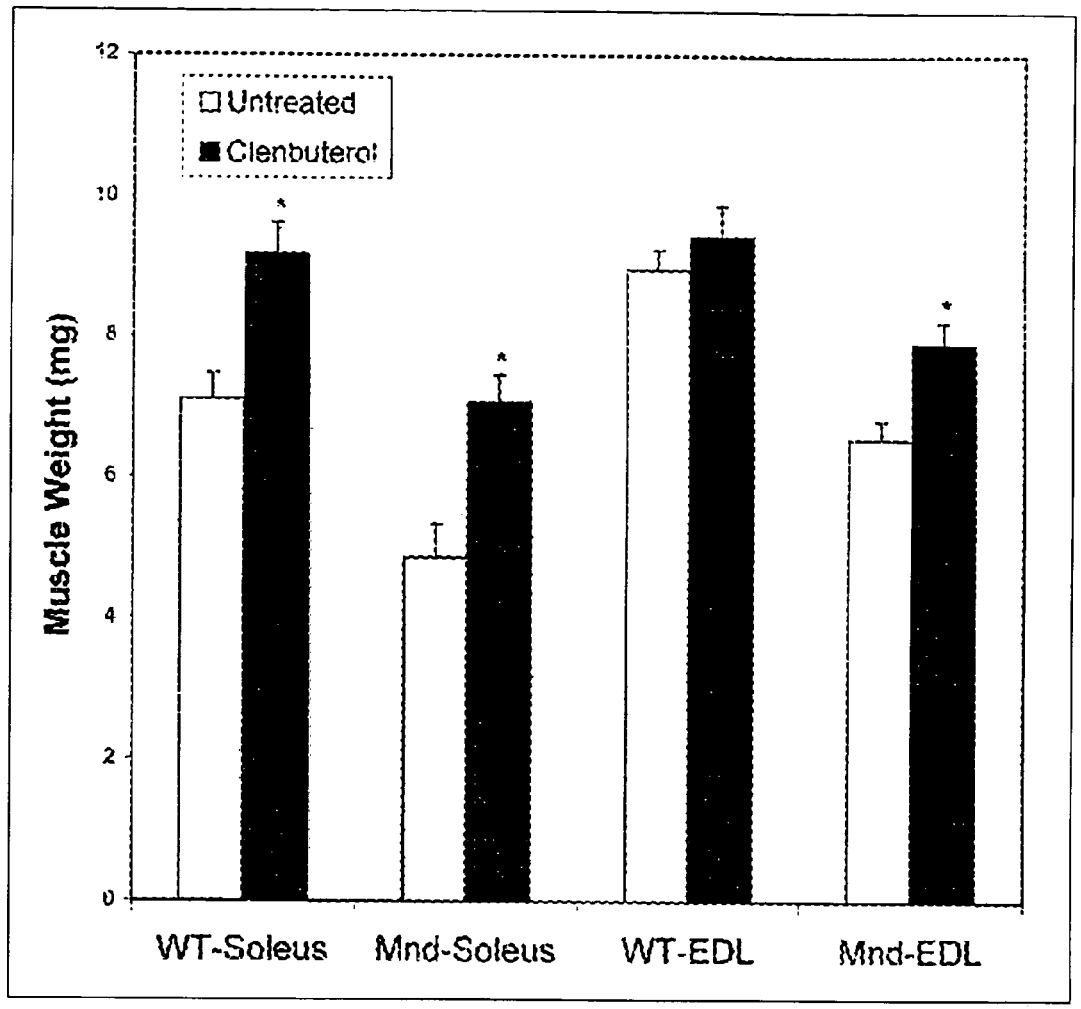

FIG. 7 shows the effects of muscle weight, relating to locomotor deficits, in the mice of FIG. 6.

Figure 8:
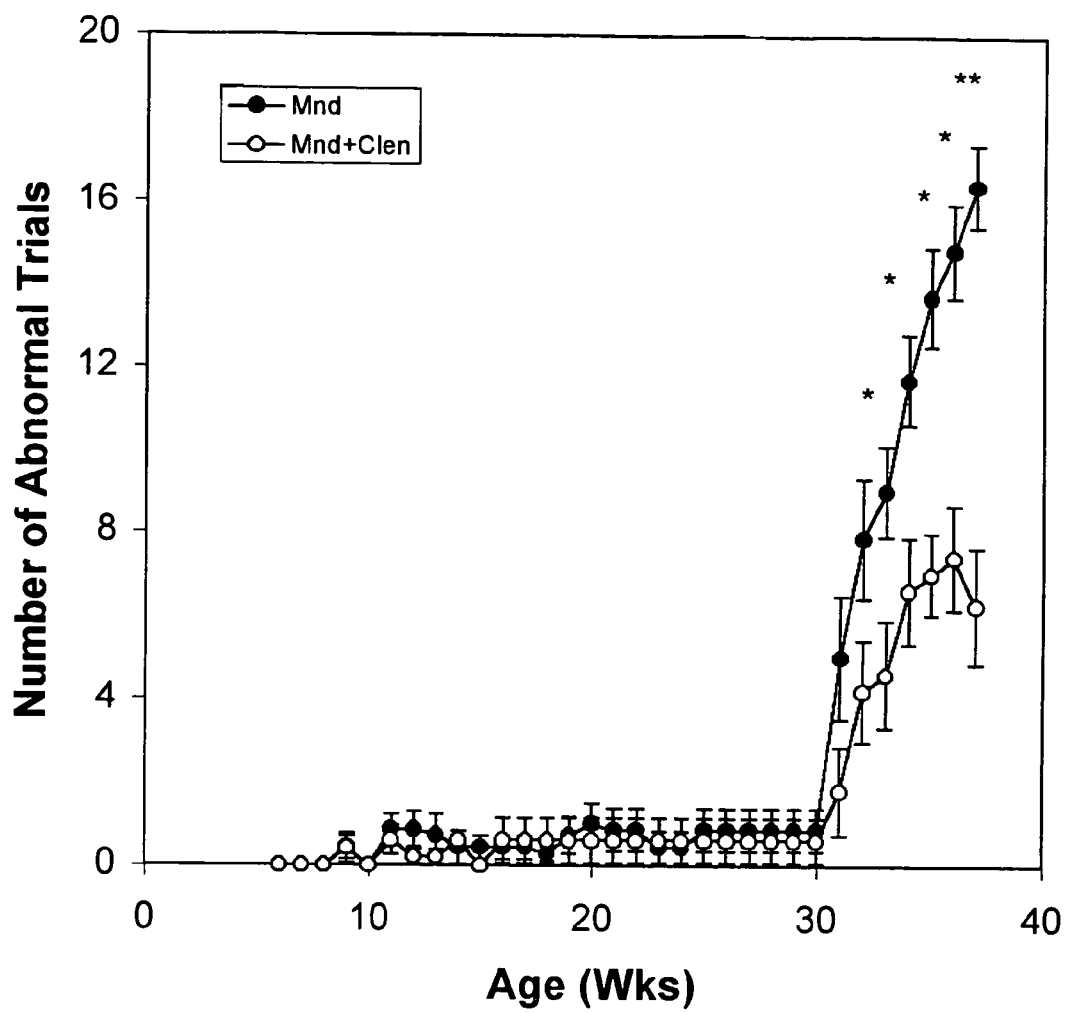

FIG. 8 is a graph showing the mean number of abnormal trials occurring in clenbuterol treated (n=5) and untreated (n=7) in the mice of FIG. 6.

Figure 9:
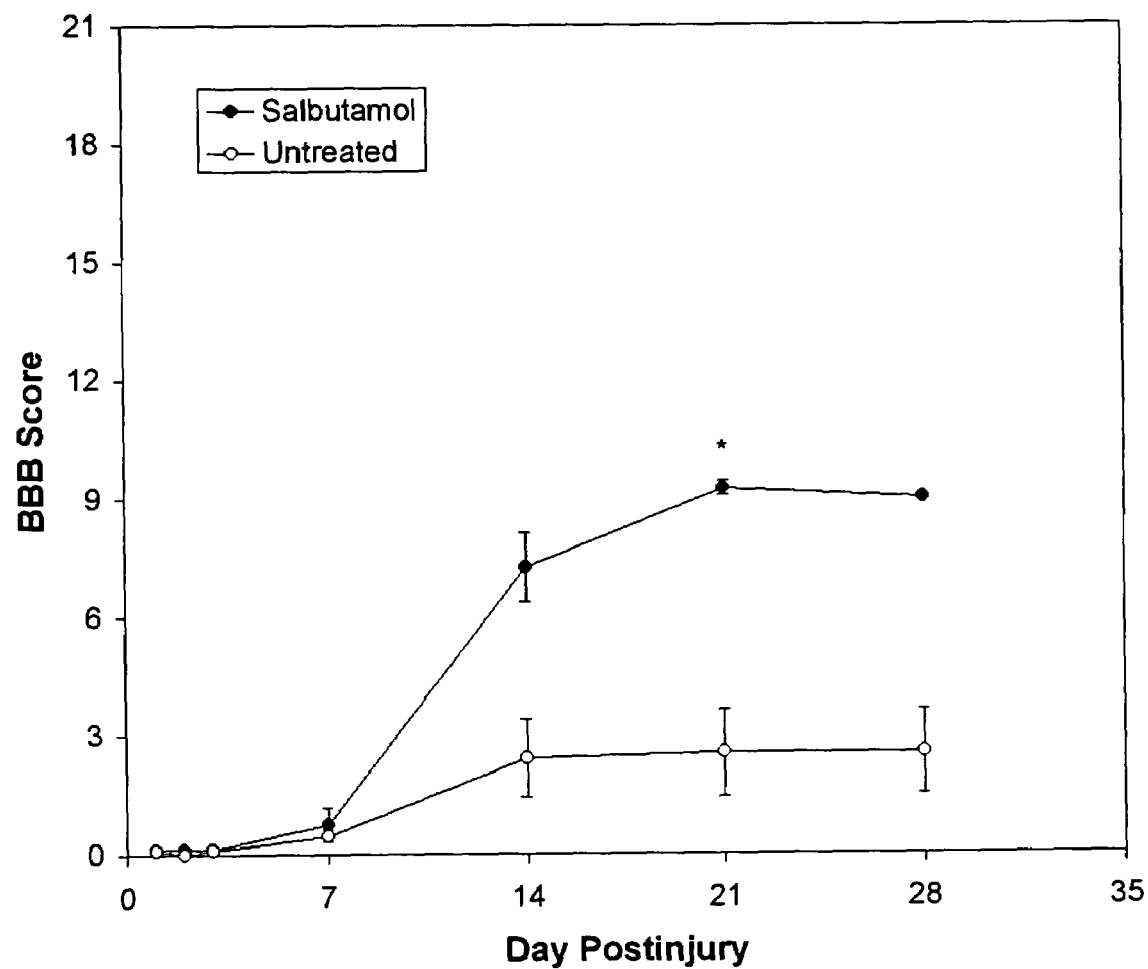

FIG. 9 shows the effects of salbutamol on locomotor function following spinal cord injury.

DETAILED DESCRIPTION OF THE PREFERRED EMBODIMENTS

An important goal of rehabilitation following spinal cord injury and treatment of degenerative neural conditions is recovery of locomotor function and neuromuscular strength. It has been determined that $\beta_2$-Adrenoceptor agonists, or simply $\beta_2$-agonists, can improve recovery of locomotor function following spinal cord injury or the results of degenerative conditions.

To quantify these effects on spinal cord injuries, a model of spinal cord injury was examined in which four graded levels of contusion injury were produced in rats at the level of T10 with a weight-drop device. Locomotor recovery was determined with the Basso, Beattie and Bresnaham (BBB) scale described in Basso, D. M., Beattie, M. S. and Breslmahan, I. C. 1995, A sensitive and reliable locomotor rating scale for open field testing in rats, J. Neurotrauma 12:1–21, incorporated by reference, which distinguishes between 22 progressive levels of recovery. It was observed that recovery during the six weeks following injury was inversely related to the severity of injury. However, administration of therapeutically effective amounts of $\beta_2$-agonists caused substantial enhancement of recovery of locomotor function at the two most severe levels of injury (BBB scores 10–12 vs 2–4). In addition, the extent of recovery was directly related to sparing of spinal cord tissue at the contusion center in both untreated and clenbuterol-treated spinal cords.

It was determined that $\beta_2$-agonists can improve recovery of locomotor function following contusion, which is thought to be the most common type of spinal cord injury. A model of spinal cord injury was examined in groups of rats in which four graded levels of contusion injury were produced with an impactor similar to the NYU weight-drop device described in Gruner, J. A 1992, A monitored contusion model of spinal cord injury in the rat, J. Neurotrauma 9:123–128, incorporated by reference. Locomotor recovery was determined during weekly observation periods with the Basso, Beattie and Bresnahan (BBB) scale. These investigators have shown that in spinal cord contused rats, 22 distinct stages of recovery can be observed that are progressive. Recovery was found to be inversely related to the severity of injury and directly related to the extent of sparing of spinal cord tissue at the contusion center. In the present study, $\beta_2$-agonists were found to dramatically improve locomotor recovery in contused spinal cords in a manner which appears related to sparing of myelinated spinal cord tissue.

$\beta_2$-adrenoceptor agonists ($\beta_2$-agonists) are a class of compounds which have the same effect as the hormone epinephrine (adrenaline) binding to the adrenergic receptors found in smooth and skeletal muscle, nervous tissue, and bronchioles. Unlike epinephrine, $\beta_2$-agonists activate primarily the $\beta_2$ receptor, not the $\beta_1$ receptor, thus avoiding some of the "fight-or-fight" effects of epinephrine, such as increased heartrate. Because of their effect on bronchioles, $\beta_2$-agonists are well known for treating asthma. Additional characteristics of $\beta_2$-agonists can be found in U.S. Pat. No. 6,015,837, incorporated herein by reference.

Known $\beta_2$ agonists include the known compounds clenbuterol, salmeterol, ractopamine, salbutamol (albuterol), cimaterol, BRL-47672, terbutaline, fenoterol, metaproterenol, isoprenaline, MJ-9184-1, trimetoquinol, tetrahydropapaveroline, soterenol, salmefamol, rimitarol, QH-25, isoetharine, R-804, orciprenaline, quinterenol, sulfonterol, dobutamine, and isoproterenol and their salts. Preferred $\beta_2$ agonists are clenbuterol, salmeterol, ractopamine, salbutamol, cimaterol, BRL-47672, terbutaline, fenoterol, metaproterenol, and isoprenaline. A particularly preferred $\beta_2$ agonist is clenbuterol. Another is salbutamol. These compounds may be used as racemates or enantiomers.

These known compounds are based on the chemical structure of epinephrine. As can be seen from their structures, these $\beta_2$ agonists are modified catecholamines having the structural features common to this group, specifically a terminal phenyl ring substituted with an aliphatic chain including an amine and a hydroxyl group. The known $\beta_2$ agonists useful in this invention may be in the form of racemic mixtures or in the form of isolated enantiomers.

The above-described $\beta_2$ agonists of this invention are known and can be obtained by the skilled person by conventional methods of chemical synthesis from readily available reagents. Many of these compounds are also commercially available from chemical suppliers (see the Merck Index). For example, clenbuterol may be obtained as described in U.S. Pat. No. 3,536,712 (incorporated herein by reference). Clenbuterol is also commercially available from Boehringer Ingelheim and Sigma Chemicals. Enantiomers of 82 agonists such as clenbuterol may be obtained by methods known to the skilled chemist and are contemplated by this invention.

Of course, there may be other known or presently unknown compounds having $\beta_2$ agonist activity which may or may not be chemically similar to those described above, and all such compounds and their use would be within the scope of the present invention.

$\beta_2$ agonists are compounds which prevent stimulation of $\beta_1$ adrenergic receptors found on skeletal and smooth muscles. These receptors are responsible for causing increased heart rate and other well-known effects of the "fight-or-flight" adrenergic response. Mixed $\beta$ blockers prevent stimulation of both $\beta_2$ and $\beta_2$ adrenergic receptors.

To determine whether a compound for use in this invention has antagonistic activity, assays known to a skilled person may be performed. For example with regard to $\gamma_2$ agonistic activity, the assay described above for measuring $\beta_2$ agonistic activity may be used, if a compound reduces or blocks the activity of an agonist, then it has antagonistic activity. With regard to $\beta_1$ activity, assays for this are well known. For example, an antagonist will decrease the heartrate of an experimental animal whose heartrate has been stimulated. A similar assay may be performed with blood pressure, which will be decreased by an antagonist. A mixed $\beta$ blocker will have both activities. An active compound may be a racemate or enantiomer or in salt form.

A number of specific $\beta_2$ agonists and mixed B blockers are well known in the art. See, for example, the Physician's Desk Reference, 51st ed. 1997 (PDR). Exemplary $\beta_1$ antagonists include CGP 20712 (Sillence 1995), and atenolol and metoprolol (PDR pp. 2963, 560, Merck Index). An example of a mixed $\beta_2$ blocker is propranolol (PDR p. 2834, Merck Index).

Method of Treatment

The method of this invention provides for administration of a $\beta_2$ adrenergic agonist to a mammalian patient with an injury to the spinal cord or a neural condition, leading to loss of locomotor activity, in an amount effective to treat and improve the injury or condition. As discussed above, compounds having the activity of a $\beta_2$ agonist is useful in this invention.

An effective amount of $\beta_2$ agonist is an amount which significantly improves neural and/or opposes neural degeneration and/or enhances locomotor function. This is readily established by a skilled practitioner based on before and after comparisons of the patient's condition using any known means. Thus the skilled practitioner can administer a minimal starting dose of $\beta_2$ agonist to a patient and monitor the patient's condition. If improvement is noted, then the same dose can be repeated. If not, the dose ran be increased until improvement occurs, then that effective dose can be used for further treatment. Once the condition or injury is sufficiently ameliorated, the practitioner can determine whether to discontinue the treatment, or possibly to continue on a maintenance or prophylactic basis.

Determination of a minimal dose for hormone agonists such as those of this invention is known to a skilled practitioner. $\beta_2$ agonists such as clenbuterol are known as asthma medications. In addition, clenbuterol in particular is known to be a long-lasting medication which is effective in low and high doses. The other $\beta_2$ agonists which are not long lasting would be more effective at higher or more frequent doses.

Specific dosage regimens for $\beta_2$ agonists in the method of this invention are from about 0.5 to about 1000.0 µg/kg/day. A range of from about 10.0 to about 100.0 µg/day is particularly effective, and about 40 µg/day is most effective. Thus, for example, clenbuterol may be administered in doses of from about 0.5 to about 1000.0 µg/kg/day, and in particular from about 10.0 to about 100.0 µg/day. The skilled practitioner will be able to adjust the dosage as appropriate to the specific situation. If more than one $\beta_2$ agonist is administered in one dose, then the dosages of each should be adjusted (downward) accordingly. Single, one time treatments have been found to be effective.

Treatment can be accomplished by including the $\beta_2$ agonists in known carriers or in liquid compositions as will be well understood in the art. Administration through liquid solution, slow release or ordinary tablets of various sizes and doses will be effective.

Experimental Methods

Adult female Wistar rats (~245 g) were obtained from Charles River Breeding Laboratories and housed in a temperature-regulated (23° C.) animal facility. The spinal cords were contused with a weight drop apparatus similar to the NYU impactor (See also Basso, D. M., M. S. Beattie, and I. C. Breslmahan, 1996, Graded histological and locomotor outcomes after spinal cord contusion using the NYU weight-drop device versus transection, Exp. Neurol. 139:244–256, incorporated by reference) at the level of T10. Prior to surgery, the rats were anesthetized with an injection of pentobarbital sodium (60 mg/kg ip) and laminectomy was performed aseptically at T9–T10 to expose the spinal cord. The spinous processes at T8 and T11 were fixed with clamps to prevent movement during contusion. Body temperature was maintained at 37° C. during the period of anesthesia with a temperature-controlled heating pad and rectal thermometer. Graded injuries were produced in groups of rats by dropping a 10 g rod with a tip diameter of 2.5 mm from heights of either 6.25, 12.5, 25 or 50 mm as in the experiments of Basso identified above. Following contusion, each incision was closed with woundclips. An additional four groups of identically contused rats received clenbuterol received (from Chinoin, Mexico City) that was administered by adding it to the drinking water at a dose of 9 mg/L. This concentration delivers clenbuterol at a rate of 1.6 mg/kg body wt./day. The animals had access to water and food in their cages immediately after recovery from surgery and throughout the experiment. Water consumption is not believed to be affected by the addition of clenbuterol. Oral dosing is particularly effective over prolonged periods because clenbuterol readily enters the circulation via the gut, has high receptor affinity and a relatively long half-life. In all, 8 treatment groups (Table I) were examined. All of the procedures involving vertebrate animals were approved by the Institutional Animal Care and Use Committee of New York Medical College.

TABLE 1

Body weights of spinal cord contused and clenbuterol-treated rats.

| Weight Drop Height, mm | Clen-buterol ± | No. of Rats | | | Initial Body Wt, gm | Final Body Wt, gm |
|---|---|---|---|---|---|---|
| | | Total | Survivors 3 Wk | 6 Wk | | |
| 6.25 | − | 8 | 7 | 6 | 244 ± 4 | 277 ± 7 |
| 6.25 | + | 8 | 8 | 8 | 244 ± 2 | 340 ± 11 |
| 12.5 | − | 13 | 10 | 9 | 248 ± 5 | 273 ± 9 |
| 12.5 | + | 13 | 12 | 11 | 250 ± 3 | 331 ± 6 |
| 25 | − | 12 | 12 | 10 | 242 ± 3 | 234 ± 10 |
| 25 | + | 10 | 10 | 8 | 246 ± 4 | 303 ± 8 |
| 50 | − | 14 | 11 | 7 | 242 ± 2 | 240 ± 12 |
| 50 | + | 14 | 13 | 10 | 247 ± 4 | 290 ± 8 |

Table I values are means±SE of measurements of body weight. Body weights were obtained immediately before and 6 weeks after contusion of the spinal cord at T10 with a weight drop apparatus as described above. Weight drop distances of 6.25–50 mm were used to vary the severity of injury as shown. The rats were either treated with clenbuterol administered in the drinking water (9 mg/L) following injury or were untreated.

Behavioral Analysis

Recovery of locomotor function was determined with BBB scale as previously described. The scale has 22 levels which range from 0 (total paralysis) to 21 (normal locomotion). Briefly, the rats were acclimatized daily to a circular observation area three feet in diameter for a week prior to surgery. For the three days following contusion and at one week intervals thereafter for a total of six weeks, each rat was scored for locomotor function according to the BBB scale. To facilitate scoring, training materials, including a videotape of locomotor behavior corresponding to the levels of the BBB scale were kindly provided by D. Michele Basso, Ed. D. (Ohio State University). The score for each animal was assigned by two observers without knowledge of the treatment condition during a 4 minute session of open field testing. The scores for both hindlimbs were averaged to obtain the score for each session. For several rats in treatment groups receiving 50 mm weight drops, treatment conditions became known and were scored by one observer. These BBB scores were pooled with the scores obtained under blinded conditions, since there was no significant difference (P>0.8, t test). Scores of animals that that did not survive until the sixth week were eliminated. However, inclusion of the scores from non-surviving rats did not alter the effects of injury severity or clenbuterol on locomotor recovery.

Spinal Cord Histomorpometry

Following six weeks of behavioral evaluation and measurement of final body weight (Table 1), the spinal cords were fixed by transcardial perfusion in the anesthetized rats (pentobarbital sodium 60 mg/kg, ip) with phosphate buffered saline (pH 7.4) containing 1% glutaraldehyde and 4% paraformaldehyde, dissected, immersed in fresh fixative and embedded in paraffin. The spinal cords were embedded from T8 to T11 in 5 or 10 mm blocks including the contusion site, which could be visualized externally. The contusion site was sectioned throughout with a microtome at a thickness of 15 µm and stained for myelin with luxol fast blue and counterstained with cresyl violet as previously described. Quantification of the cross-sectional area of remaining intact grey and white matter relative to total cord cross-sectional area were performed with a computerized digitizing tablet (Sigmascan) from tracings of the stained section exhibiting the largest lesion from each spinal cord.

Statistical Analysis

The statistical significance of the effects of treatments were determined by analysis of variance and the least significant difference multiple range test at the P<0.05 level (SPSS 8.0). Linear regression analysis was performed with Excel 4.0. Determinations of statistical differences for comparisons between two means were determined with the Student's t test.

Behavioral Recovery

Figure 1:
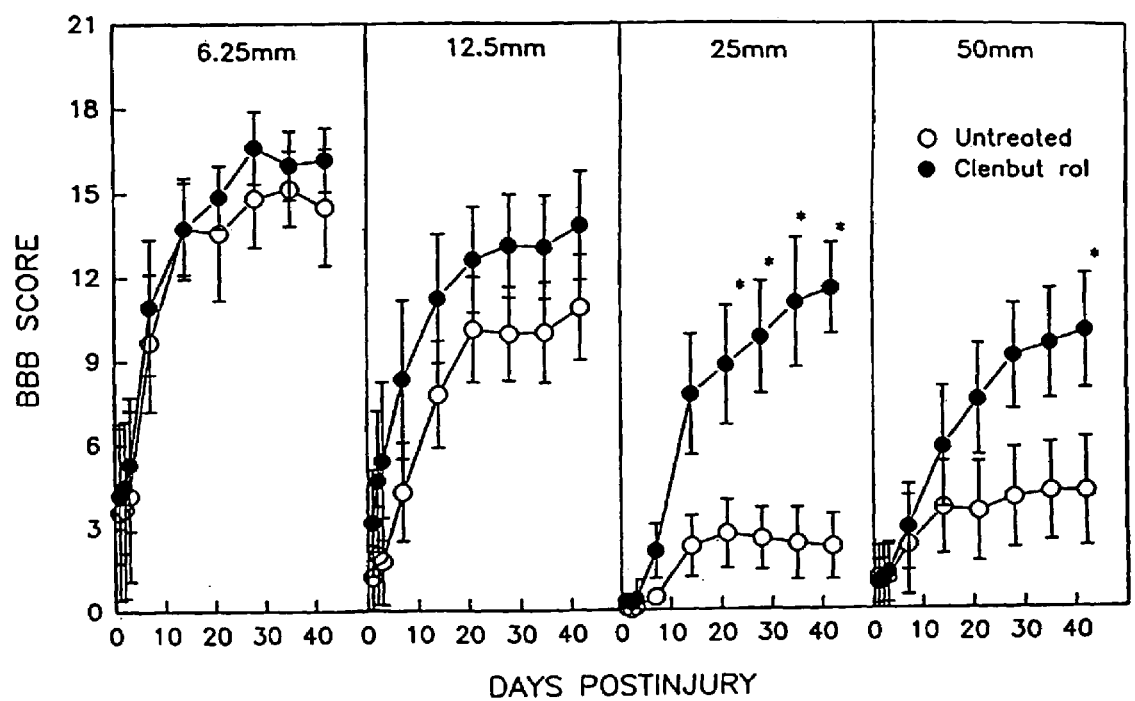
FIG. 1 is a graph showing the effects of clenbuterol on spinal cord contusion injuries of graded severity on the time course of locomotor recovery. Values are means±SE of determinations of locomotor recovery according to the BBB scale. The rats received contusion injury with either 6.25, 12.5, 25 or 50 mm weight drops and received clenbuterol treatment or were untreated and were scored as described in Methods. *$P<0.05$, significant effect of clenbuterol on BBB score compared to untreated rats receiving the same injury.
Figure 2:
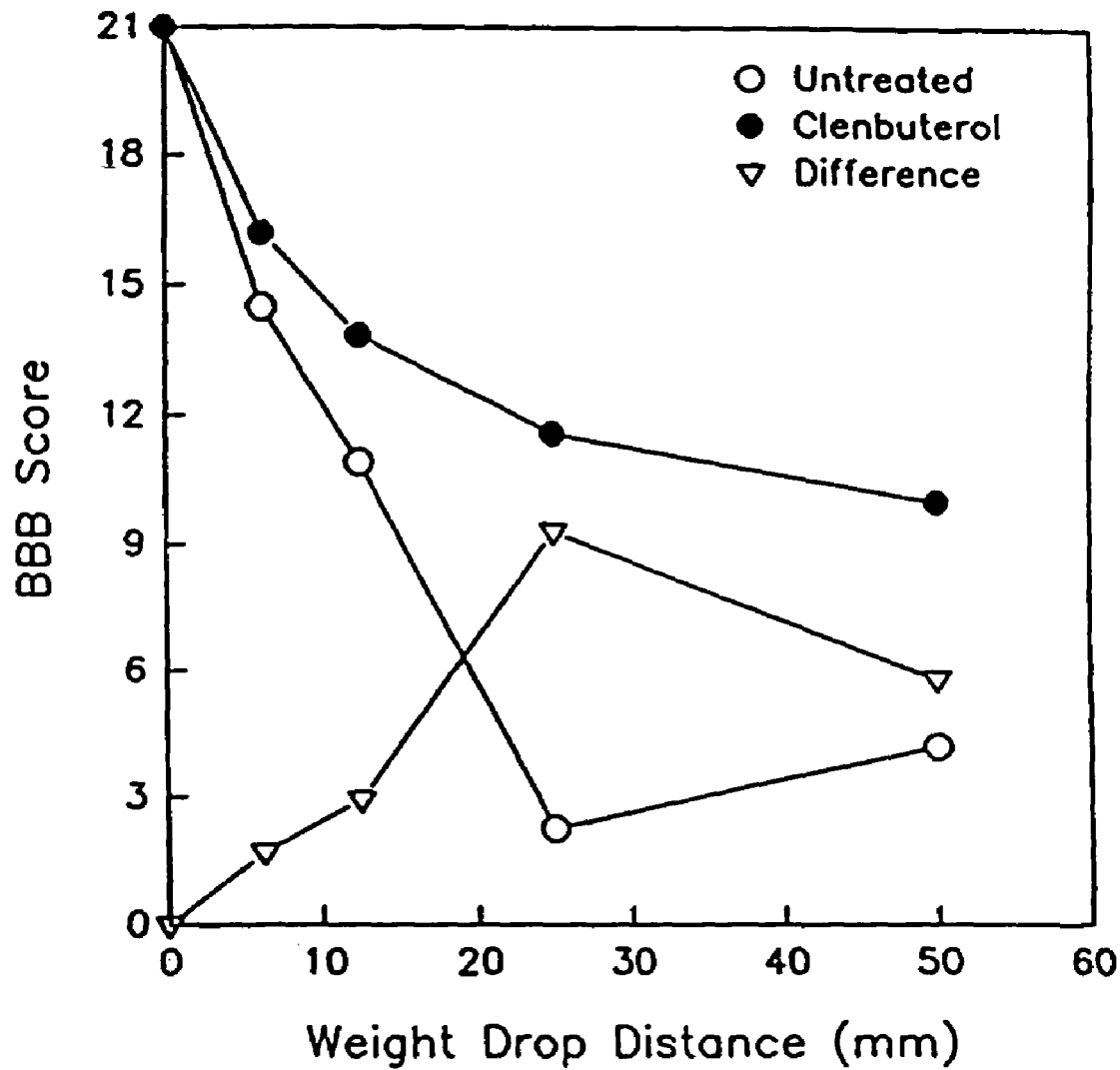
FIG. 2 is a graph showing mean final BBB scores from FIG. 1, plotted against the height of weight drop used to contuse the spinal cord, a plot of the difference in BBB scores due to clenbuterol treatment at each level of injury ($\nabla$—$\nabla$), which shows the greatest effectiveness following a weight drop of 25 mm.

Contusion injuries produced decreases in behavioral performance as measured by BBB scores, that were directly related to the height of the weight drop onto the exposed spinal cord see FIGS. 1 and 2. Recovery of locomotor function occurred within 2–3 weeks of injury to levels that were maintained for the remainder of the 6 week observation period. Contusion injuries produced by weight drops in the range of 6.25–25 mm progressively decreased final BBB scores to levels that were not further reduced by 50 mm weight drops.

Clenbuterol significantly increased the level of recovery following the four different levels of injury (FIGS. 1 and 2). The mean of the final BBB scores for the clenbuterol-treated groups was 13.2±1.5 (±SE) compared to 8.0±2.9 for the untreated groups (P<0.05, paired t-test). However, the improvements in BBB scores due to clenbuterol treatment were greater as the severity of injury increased. The greatest improvement in final BBB score (9.3 levels) due to clenbuterol was observed following a 25 mm weight drop. A significant increase was found beginning at the third week, with a tendency to increase further during the following three weeks. Significant increases in BBB score of 5.1–5.8 levels were also observed following the 50 mm weight drop at the fourth, fifth and sixth weeks of observation.

Histology

Figure 3:
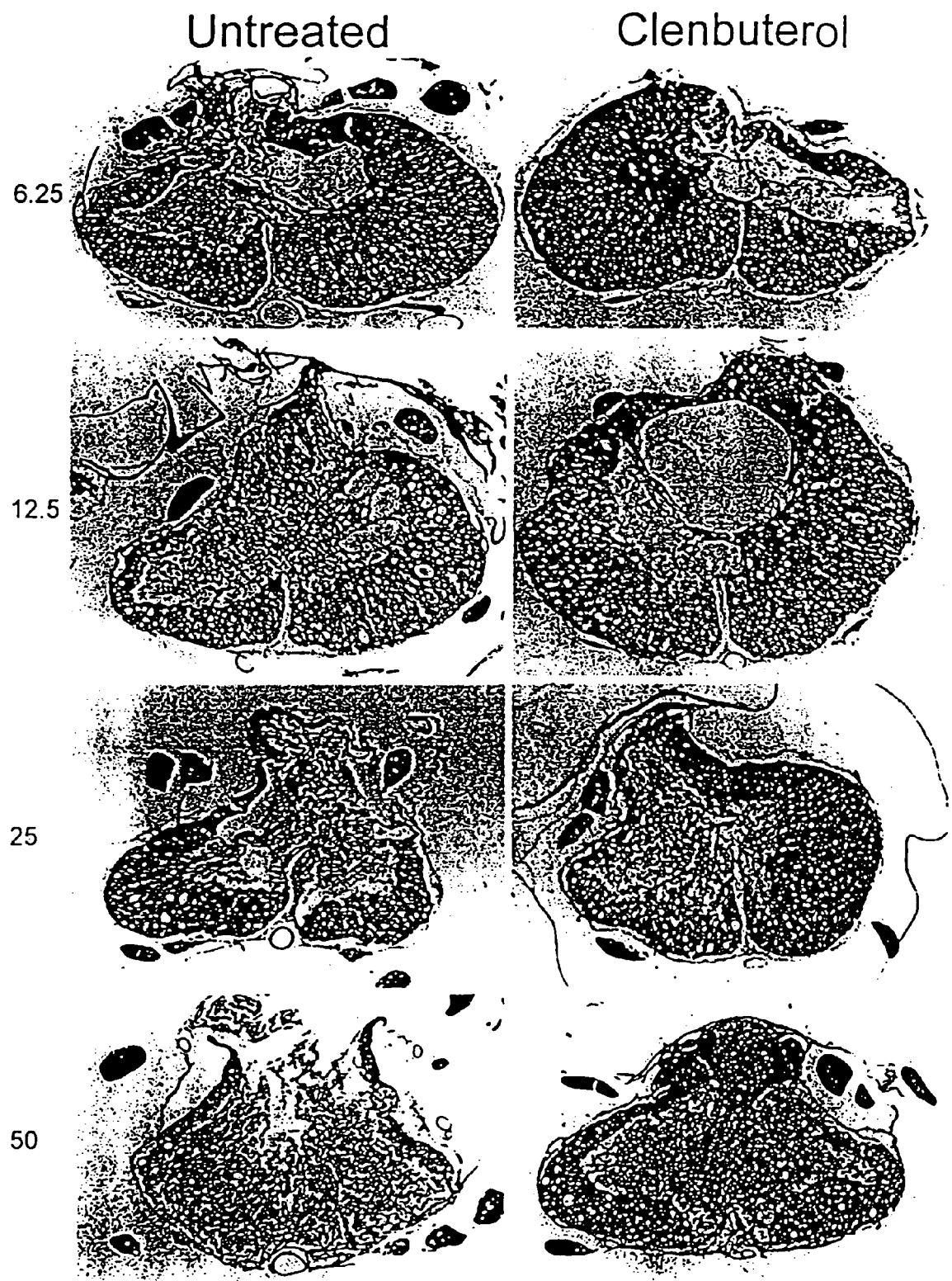
FIG. 3 is a compilation of photographs showing transverse sections of spinal cords at the contusion center from untreated (left-hand column) and clenbuterol-treated (right-hand column) rats. The rats received contusion injury with either 6.25, 12.5, 25 or 50 mm weight drops (indicated on the left) and clenbuterol treatment as described in Methods. The sections were stained with luxol fast blue for myelin and counterstained with cresyl violet. Increasing the height of the weight drop progressively caused greater damage to the spinal cord until the rim of spared tissue was greatly reduced in cross-sectional area. A greater extent of sparing of spinal cord tissue is observed 6 weeks after contusion of the clenbuterol-treated compared to the untreated spinal cords. The calibration bar equals 500 μm.

Weight-drop contusion resulted in the appearance of a centrally located lesion within the spinal cord and sparing of a peripheral rim of tissue (FIG. 3). The central lesion consisted mostly of areas of gliosis and cyst formation or cavitation and included most or all of the area previously occupied by grey matter as well as contiguous regions of white matter. The peripheral rim of spared tissue consisted of remaining white matter and in some cases small areas of grey matter including the dorsal horn. Within the spared white matter, staining with luxol fast blue indicated the presence of myelinated fibers, although there were also scattered microcysts indicating axonal injury.

Figure 4:
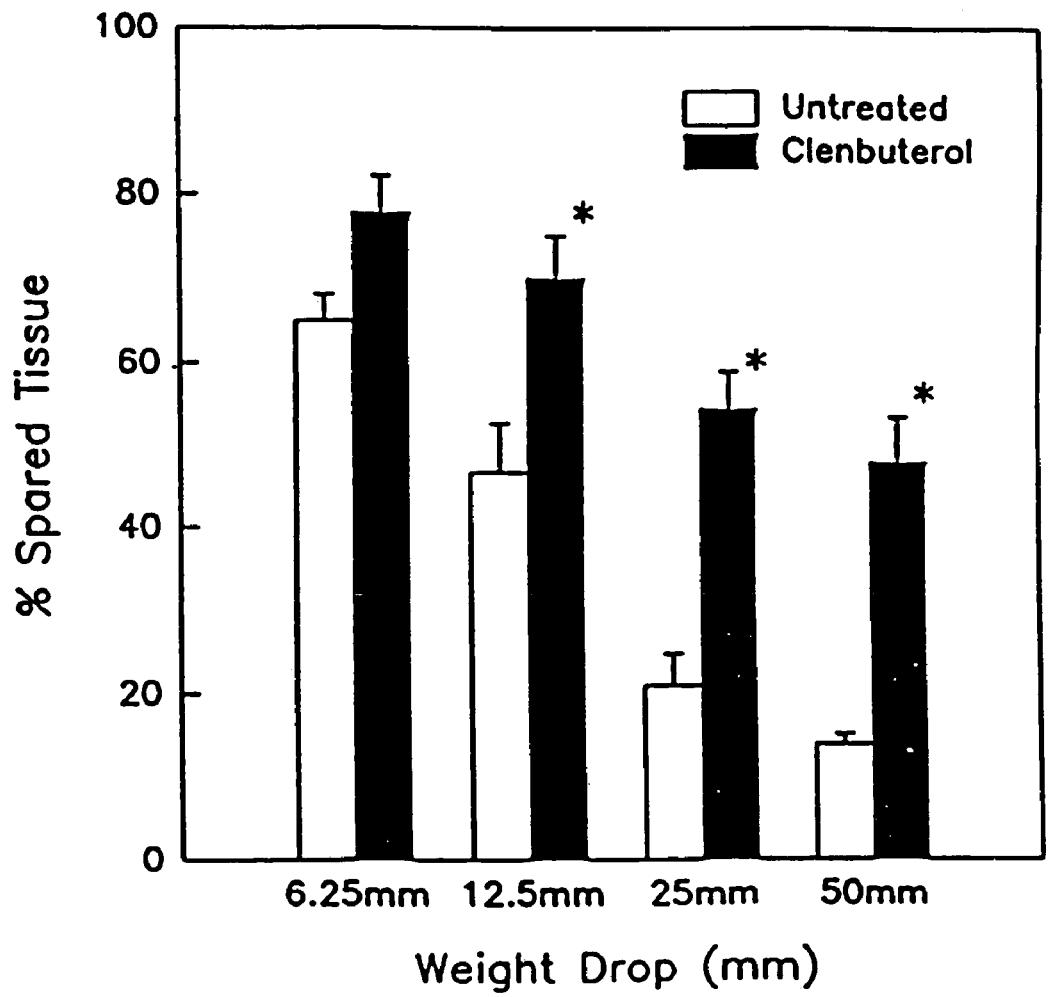
FIG. 4 is a graph showing Mean values of measurements of % spared tissue in sections of contused spinal cords obtained as in FIG. 1 Groups of rats were untreated or clenbuterol-treated and received weight drops of 6.25–50 mm as shown and measurements of % spared tissue were performed as described in Methods. *$P<0.05$, significant difference due to clenbuterol compared to the untreated group receiving the same injury.
Figure 5:
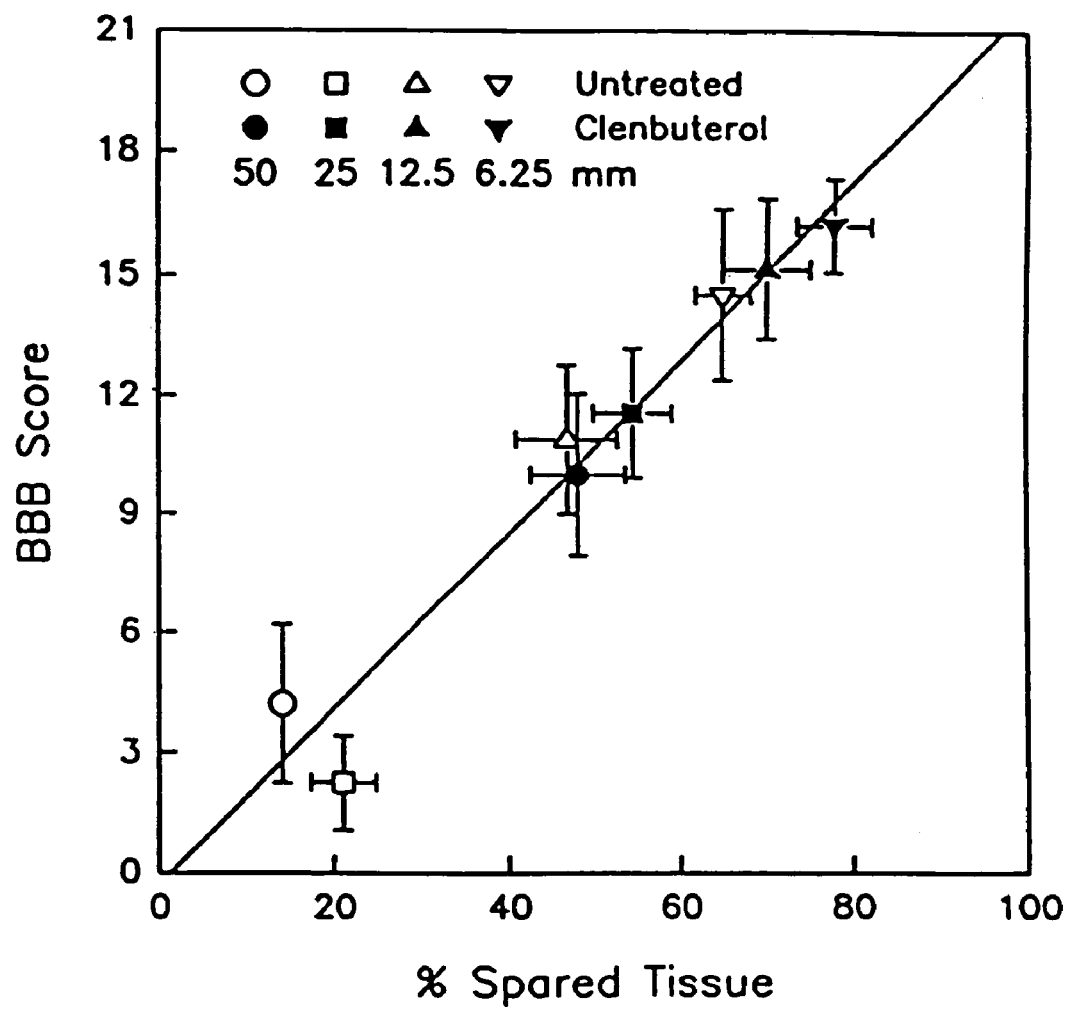
FIG. 5 is a graph showing a plot of % spared spinal cord tissue against final BBB score. Values are means±SE of % spared tissue at the contusion center and BBB scores obtained from treatment groups that were either untreated or clenbuterol-treated and received contusion injuries from weight drops of 6.25–50 mm as shown (see FIGS. 1 and 3).

Increases in the height of the weight drop resulted in progressive decreases in the amount of spinal cord tissue spared (FIGS. 3 and 4). On the other hand clenbuterol significantly increased the relative amount of spared spinal cord tissue following the three most severe weight drops. Clenbuterol treatment accounted for 23, 33, and 34% sparing of spinal cord tissue following contusion injuries from weight drops, respectively, of 12.5, 25 and 50 mm. Linear regression analysis demonstrated a significant linear relationship between the mean values of BBB score and % spared tissue (FIG. 5) for each treatment group ($r^2$=0.96, slope=0.22±0.02 BBB score/% spared tissue, P<0.0005).

It was determined that $\beta_2$-adrenoceptor agonists, such as clenbuterol, can enhance recovery of locomotor function following spinal cord contusion injury in humans and other mammals. The enhancement of recovery due to clenbuterol was associated with sparing of spinal cord tissue at the contusion center.

To determine the effects of clenbuterol a model of spinal cord contusion was examined in which four graded levels in the severity of impact were previously shown to incrementally reduce the extent of locomotor recovery. Graded injuries are produced in this model using the NYU weight drop device in which a 10 g rod impacts the exposed dura of the spinal cord after release from one of four different preset heights. In order to evaluate recovery of locomotor function, a modified and expanded version of the Tarlov scale has been developed by Basso, Beattie and Bresnahan which distinguishes between 22 levels of locomotor performance. These levels of performance were found to occur progressively during the period of recovery. The extent of locomotor recovery, in turn, was found to be directly related to the amount of tissue spared at the injury site.

Histological examination of the contusion center has shown that the central grey matter is severely affected and mostly replaced by cavitation and areas of gliosis. In addition, depending on the severity of injury, cavitation may extend into surrounding myelinated areas so that a rim of spared white matter remains. Within the spared region are essentially normal myelinated fibers, although there are also scattered microcysts indicative of axonal damage. Since spinal cord tissue loss is greatest at the center of contusion, it is likely that the extent of tissue loss at this site limits the degree of locomotor recovery. The amount of remaining white matter would determine the extent of locomotor deficit, since the myelinated axons within the spinal columns conduct activity necessary for recovery of coordinated locomotor movements as shown following transection. Experiments involving selective transection of dorsal, ventral and/or lateral funiculi, suggest that the functional roles of remaining axons are respecified to compensate for lost axons during recovery of locomotion. However, the more extensive the loss of axons, the greater the functional demand on remaining axons. The loss of axons beyond the number that provides for a safety factor results in an inability to recover completely and is a likely explanation for the quantitative relationship between the extent of recovery of locomotor function and tissue sparing.

The ability of chronic stimulation of $\beta_2$-receptors to spare injured spinal cord tissue, may represent another aspect of the well known fight or flight response in which the adrenergic axis of the stress response becomes active. The organism may adapt to stressors, e.g., predation, that increase risk of injury by releasing endogenous catecholamines that, in turn, stimulate $\beta_2$-receptors and limit tissue loss. It has been determined that continuous stimulation of $\beta_2$-receptors with a potent $\beta_2$-agonist such as clenbuterol should mimic and enhance effects of the stress response mediated by the $\beta_2$-receptor.

$\beta_2$-adrenoceptors such as clenbuterol may act by stimulating the release of factors that have neuroprotective properties. Clenbuterol has been found to exert neuroprotective effects on hippocampal neurons following ischemia. In in vitro experiments, clenbuterol caused the release of NGF, which protected cultured hippocampal neurons from glutamate excitotoxicity. The ability of growth factors to preserve neuronal populations has also been demonstrated in experiments in which hippocampal neurons were protected by FGF from glutamate excitotoxicity. Increased growth factor expression can also promote neurite outgrowth, which may lead to altered patterns of synaptogenesis important for respecifying axonal function during recovery. Interestingly, treatment of a cortical neuron cell line with a $\beta_2$-receptor agonist, directly stimulates neurite outgrowth. Agents that increase neuronal cAMP levels, a defining action of $\beta_2$-agonists, can enhance rates of regeneration following crush of peripheral nerve. It has also been demonstrated that clenbuterol reduced infarct volume due to brain ischemia.

Clenbuterol may also spare spinal cord tissue following contusion by altering expression of other factors such as cytokines. Studies of cultured astrocytes have demonstrated that stimulation of $\beta_2$-receptors causes secretion of interleukin-6. (IL-6) Administration of IL-6, has been shown to improve locomotor function following spinal cord compression injury. Astrocytes contain abundant $\beta_2$-receptors that would be stimulated by clenbuterol which crosses the blood-brain barrier. IL-6 released in response to fu-receptor stimulation may, in turn, exert neuroprotective effects by a variety of mechanisms. For example, IL-6 binds to the gp130 family of receptors, which are found on oligodendrocytes. It has been found that ciliary neurotrophic factor (CNTF), which also binds gp130 receptors, opposes toxic effects of tumor necrosis factor-alpha (TNF-$\alpha$) on oligodendrocytes and thereby may antagonize demyelination. In this regard, TNF-$\alpha$levels in the spinal cord are elevated following contusion. IL-6, in common with CNTF, can also preserve populations of motoneurons lost due to axotomy or motor neuron disease in wobbler mice and prevents death of PC12 cells due to calcium overload. It has been found that clenbuterol greatly increases secretion of IL-6. However, the relevance of these observations regarding the release of cytokines or growth factors for recovery from spinal cord injury is not known. Regardless of the mechanism of action, $\beta_2$-agonists such as clenbuterol substantially improve locomotor function and spared spinal cord tissue following contusion, although recovery was not complete. Further optimization of the use $\beta_2$-agonists either alone or in combination with additional agents may further increase recovery from contusion injury.

To confirm that salbutamol, a $\beta_2$-adrenoceptor agonist, can enhance recovery of locomotor function following spinal cord injury. Groups of untreated and salbutamol-treated rats were evaluated with the 21 point Basso, Beattie and Bresnahan (BBB) scale (FIG. 9) following spinal cord contusion with a weight-drop device (10 g, 25 mm drop), Salbutamol was administered via subcutaneously implanted osmotic minipumps (Alzet) that delivered 1 mg/kg body weight/day during the 28 day recovery period. Recovery of locomotor function was significantly greater (*P<0.05, t test) in salbutamol-treated compared to untreated control rats. It believed that dosages of $\beta_2$-adrenoceptor agonists such as clenbuterol or salbutamol greater than 25 mg/kg body weight per day will also show therapeutic benefits in mammals, including humans, in terms of increasing locomotor function and neuromuscular strength for treatment of injury or degenerative conditions such as Mnd.

Because locomotor recovery was similar to that observed in experiments with another, $\beta_2$-adrenoceptor agonist, clenbuterol, the efficacy of this class of agents is believed to be confirmed. It was determined that $\beta_2$-adrenoceptor agonists, such as clenbuterol and salbutamol can oppose irreversible loss of neuromuscular strength and locomotor function due to motoneuron degeneration.

The effects of clenbuterol on locomotor deficits were examined in motor neuron degeneration (Mnd) mice, which exhibit progressive motoneuron degeneration. Forelimb and hindlimb grip strength was measured in groups of Mnd and wild type (WT) mice that were either treated with clenbuterol in the drinking $H_2O$ (9 mg/L) until 37 weeks of age or were untreated. Forelimb and hindlimb grip strength was reduced 44–66% in Mnd compared to WT mice (FIG. 6). Clenbuterol caused relative increases in forelimb grip strength that were greater in Mnd (75%) compared to WT (20%, P<0.05, t test) mice. In addition, clenbuterol increased hindlimb grip strength 29% in Mnd mice, but did not significantly affect hindlimb strength in WT mice. These effects of genotype and clenbuterol treatment were paralleled by similar changes in muscle mass. Thus the hindlimb soleus and extensor digitorum longus muscles were reduced 27–32% in Mnd compared to WT mice (FIG. 7). Clenbuterol caused relative increases of 46% and 29% in soleus weight in Mnd and Wt mice, respectively. In addition, clenbuterol increased extensor digitorum longus muscle weight 21% in Mnd mice, but not in WT mice.

Behavioral tests developed by Messer and Flaherty in their original description of the Mnd mice were also performed. As described in their publication (J. Neurogenetics 3:345–355, 1986), incorporated by reference, five tests of different aspects of walking and hindlimb splaying are run each week with 10 trials for each test for a total of 50 trials. The mean number of abnormal trials occurring in clenbuterol-treated (n=5) and untreated (n=7) Mnd mice were determined until the mice were 37 weeks of age at the end of the experiment (FIG. 8). Beginning at 31 weeks of age, there is a marked worsening of behavioral scores. However, the clenbuterol-treated group performed significantly better than the untreated group with a greater than two-fold difference in the mean number of abnormal trials (16.4±1.2 vs 6.3±1.6, P<0.01). Motoneuron counts in the lumbar spinal cord were not significantly reduced in Mnd mice or affected by clenbuterol. However, the percentage of motoneurons, exhibiting abnormal eccentric nuclei, was elevated to 12.6±0.9% in Mnd compared to 2.3±0.2% in WT mice. The frequency of abnormal motoneurons in each mouse was highly correlated with locomotor scores. Clenbuterol reduced the frequency of abnormal motoneurons to 8.3±0.7% (P<0.015) indicating a neurotrophic effect of $\beta_2$-agonist treatment. These results indicate that $\beta_2$-agonist treatment can be a useful therapeutic modality for motor neuron degenerative diseases such as amyotrophic lateral sclerosis (ALS) and spinal muscular atrophies (SMA).

What is claimed is:

1. A method of increasing locomotor function and/or neuromuscular strength in a mammalian patient with spinal cord contusion injury or motor neuron degeneration, the method comprising administering to the patient an amount of at least one $\beta_2$ adrenergic agonist effective to increase locomotor function and/or neuromuscular strength in the patient, wherein the $\beta_2$ adrenergic agonist is selected from the group consisting of salmeterol, ractopamine, cimaterol, terbutaline, fenterol, memproterenol, isoprenline, MJ-9184-1, trimetoquinol, tetrahydropapaveroline, soterenol, salmefamol, rimiterol, OH-25, isoetharine, R-804, orciprenaline, quinterenol, sulfonterol, dobutamine, and isoproterenol and salts of the foregoing.

2. The method of claim 1 wherein the $\beta_2$ adrenergic agonist is selected from the group consisting of salmeterol, ractopamine, cimaterol, terbutaline, fenterol, memproterenol and isoprenline and salts of the foregoing.

3. A method of increasing locomotor function and/or neuromuscular strength in a mammalian patient with spinal cord contusion injury or motor neuron degeneration, the method comprising administering to the patient an amount of at least one $\beta_2$ adrenergic agonist effective to increase locomotor function and/or neuromuscular strength in the patient, wherein the $\beta_2$ adrenergic agonist comprises clenbuterol or a salt thereof.

4. A method of increasing locomotor function and/or neuromuscular strength in a mammalian patient with contusion injury to the lower thoracic spine, the method comprising administering to the patient an amount of at least one $\beta_2$ adrenergic agonist effective to increase locomotor function and/or neuromuscular strength in the patient.

5. The method of claim 4, wherein the $\beta_2$ adrenergic agonist is selected from the group consisting of salmeterol, ractopamine, cimaterol, terbutaline, fenterol, memproterenol, isoprenline, MJ-9184-1, trimetoquinol, tetrahydropapaveroline, soterenol, salmefamol, rimiterol, QH-25, isoetharine, R-804, orciprenaline, quinterenol, sulfonterol, dobutamine, and isoproterenol and salts of the foregoing.

6. The method of claim 4 wherein the $\beta_2$ adrenergic agonist is selected from the group consisting of salmeterol, ractopamine, cimaterol, terbutaline, fenterol, memproterenol and isoprenline and salts of the foregoing.

7. A method of increasing locomotor function and/or neuromuscular strength in a mammalian patient with contusion injury to the lower thoracic spine, the method comprising administering to the patient an amount of at least one $\beta_2$ adrenergic agonist effective to increase locomotor function and/or neuromuscular strength in the patient, wherein the $\beta_2$ adrenergic agonist comprises clenbuterol or a salt thereof.

8. The method of claim 4 wherein the $\beta_2$ adrenergic agonist comprises salbutamol or a salt thereof.

9. The method of claim 1, wherein the effective amount of the $\beta_2$ adrenergic agonist is from about 10 to about 100 µg per kg of body weight.

10. The method of claim 1, wherein the effective amount of the $\beta_2$ adrenergic agonist is about 40 µg per kg of body weight.

11. The method of claim 4 wherein the effective amount of the $\beta_2$ adrenergic agonist is from about 0.5 to about 1000 µg per kg of body weight.

12. The method of claim 7 wherein the effective amount of clenbuterol is from about 0.5 to about 1000 µg per kg of body weight.

13. The method of claim 7, wherein the effective amount of clenbuterol is greater than about 0.25 mg/day per kg body weight.

14. The method of claim 1, wherein the $\beta_2$ adrenergic agonist is effective to reduce injury-induced loss of spinal cord tissue.

15. The method of claim 4, wherein the $\beta_2$ adrenergic agonist is effective to reduce injury-induced loss of spinal cord tissue.

16. The method of claim 4, wherein the effective amount of the $\beta_2$ adrenergic agonist is from about 0.5 to about 100 µg per kg of body weight.

17. The method of claim 1, wherein the effective amount of the $\beta_2$ adrenergic agonist is from about 0.5 to about 100 µg per kg of body weigh.

18. A method of increasing locomotor function and neuromuscular strength in a mammalian patient with spinal cord contusion injury to the lower thoracic spine, the method comprising administering to the patient an amount of at least one $\beta_2$ adrenergic agonist effective to increase locomotor function and neuromuscular strength in the patient, wherein the $\beta_2$ adrenergic agonist is selected from the group consisting of salmeterol, ractopamine, cimaterol, terbutaline, fenterol, memproterenol, isoprenline, MJ-9184-1, trimetoquinol, tetrahydropapaveroline, soterenol, salmefamol, rimiterol, QH-25, isoetharine, R-804, orciprenaline, quinterenol, sulfonterol, dobutamine, clenbuterol, salbutamol and isoproterenol and salts of the foregoing.

19. The method of claim 8 wherein the effective amount of salbutamol is from about 0.5 to about 1000 µg per kg of body weight.

20. The method of claim 8, wherein the effective amount of salbutamol is greater than about 0.25 mg/day per kg body weight.

* * * * *